United States Patent [19]

Sehgal et al.

[11] Patent Number: 5,206,018
[45] Date of Patent: Apr. 27, 1993

[54] USE OF RAPAMYCIN IN TREATMENT OF TUMORS

[75] Inventors: Surendra N. Sehgal, Princeton, N.J.; Claude Vezina, Oka, Canada

[73] Assignee: Ayerst, McKenna & Harrison, Inc., St. Laurent, Canada

[21] Appl. No.: 784,274

[22] Filed: Oct. 29, 1991

Related U.S. Application Data

[60] Continuation-in-part of Ser. No. 682,813, Apr. 9, 1991, Pat. No. 5,066,493, which is a continuation-in-part of Ser. No. 391,334, Aug. 9, 1989, abandoned, which is a division of Ser. No. 592,193, Mar. 22, 1984, Pat. No. 4,885,171, which is a continuation of Ser. No. 126,276, Mar. 3, 1980, abandoned, which is a continuation of Ser. No. 957,626, Nov. 3, 1978, abandoned.

[51] Int. Cl.$^5$ .............. A61K 35/00; A61K 31/66; A61K 31/505; A01N 57/00
[52] U.S. Cl. .................... 424/122; 514/110; 514/274; 514/291
[58] Field of Search ............ 424/122; 514/110, 274, 514/291

[56] References Cited

U.S. PATENT DOCUMENTS

| | | | |
|---|---|---|---|
| 3,929,992 | 2/1976 | Sehgal | 424/122 |
| 3,993,749 | 11/1976 | Sehgal | 424/122 |
| 4,316,885 | 3/1982 | Rakhi | 424/122 |
| 4,401,653 | 8/1983 | Eng | 424/114 |
| 4,650,803 | 3/1987 | Stella et al. | 514/291 |
| 4,885,171 | 12/1989 | Surendra et al. | 424/122 |
| 5,066,493 | 11/1991 | Sehgal | 424/122 |
| 5,078,999 | 1/1992 | Warner | 424/122 |
| 5,080,899 | 1/1992 | Sturm | 424/122 |

OTHER PUBLICATIONS

U.S. patent application. Ser. No. 07/717,773 filed Jun. 18, 1991—(Miller).
Abst. dist. at Fifth Intl Conf. of Inflamm. Res. Assoc. 121, Sep. 23, 1990 (Baeder, W. L.).
Vezina, C. J. Antibiot. 28, 721–726 (1975).
Sehgal, S. J. Antibiot. 28, 727–732 (1975).
Martel. R., Can J. Physiol. Pharmacol., 55, 48 (1977).
Eng. C. J. Antibiotics 37:1231 (1984).
FASEB 3:3411 (1989)—(Staruch, M. J.).
FASEB 3:5256 (1989)—(Dumont, F. J.).
Med. Sci. Res. 17:877 (1989)—(Morris, R.).

*Primary Examiner*—Nathan M. Nutter
*Attorney, Agent, or Firm*—Arnold S. Milowsky

[57] ABSTRACT

This invention provides a method of treating, inhibiting the proliferation of, reducing the size of, or eradicating malignant neoplasms in a mammal in need thereof which comprises administering an antineoplastic amount of rapamycin to said mammal. In particular, rapamycin is useful in treating, inhibiting the proliferation of, reducing the size of, or eradicating malignant mammary and skin carcinomas, and central nervous system neoplasms.

12 Claims, No Drawings

USE OF RAPAMYCIN IN TREATMENT OF TUMORS

This a continuation-in-part application of co-pending application Ser. No. 07/682,813, filed Apr. 9, 1991 and now U.S. Pat. No. 5,066,493, which in turn is a continuation-in-part application of co-pending application Ser. No. 07/391,334, filed Aug. 9, 1989 and now abandoned, which in turn is a divisional application of co-pending application Ser. No. 06/592,193, filed on Mar. 22, 1984, now issued as U.S. Pat. No. 4,885,171, on Dec. 5, 1989, which in turn is a continuation application of co-pending application Ser. No. 06/126,276, filed on Mar. 3, 1980, now abandoned, which in turn is a continuation application of co-pending application Ser. No. 05/957,626, filed Nov. 3, 1978, now abandoned.

BACKGROUND OF THE INVENTION

1. Field of the Invention

This invention relates to the use of rapamycin as an anti-cancer or anti-tumor agent.

2. Description of the Prior Art

Rapamycin is an antifungal antibiotic described by C. Vezina et al., J. Antibiot., 28, 721 (1975), S. N. Sehgal et al., J. Antibiot., 28, 727 (1975) and S. N. Sehgal et al., U.S. Pat. No. 3,929,992, issued Dec. 30, 1975, filed Apr. 12, 1974. Rapamycin is extracted from a streptomycete (*Streptomyces hygroscopicus*) isolated from an Easter Island soil sample and is particularly effective against *Candida albicans* both in vitro and in vivo.

In addition, a recent report by R. R. Martel et al., Can. J. Physiol., 55, 48 (1977) describes the use of rapamycin for the prevention of the development of two experimental immunopathies [(experimental allergic encephalomyelitis (EAE) and adjuvant arthritis (AA)]. The latter report also describes the inhibitory effect of rapamycin on the formation of humoral (IgE-like) antibody. This report concludes that immunosuppressant activity of rapamycin appears to be related to inhibition of the lymphatic system.

SUMMARY OF THE INVENTION

According to this invention a method is provided for treating malignant neoplasms in a mammal which comprises administering to said mammal an antineoplastic amount of rapamycin. More specifically, rapamycin inhibits the proliferation of malignant cells, controls the growth of malignant neoplasms, reduces the size of malignant neoplasms, eradicates malignant neoplasms, prolongs the survival time of said mammal, kills malignant cells, and adversely affects malignant cells.

DETAILS OF THE INVENTION

According to the present method, rapamycin is employed as the active agent. The isolation and description of rapamycin is given in U.S. Pat. No. 3,929,992, cited above, herein incorporated by reference.

Rapamycin is administered, either orally or parenterally, to a carcinogenic tumor bearing mammal for the purpose of inhibiting the proliferation of malignant cells, controlling the growth of malignant neoplasms, reducing the size of malignant neoplasms, eradicating malignant neoplasms, prolonging the survival time of said mammal, killing malignant cells, and adversely affecting malignant cells.

While rapamycin can be administered above, e.g. as a sole component of a filled capsule, it is preferred to formulate the compound in various dosage forms for oral or parenteral administration, e.g. tablets or sterile solutions. Such formulations are described in U.S. Pat. No. 3,929,992, cited above. Rapamycin may also be administered in combination with a therapeutically effective amount of an antineoplastic agent commonly used in cancer therapy.

When the antifungal antibiotic of this invention is employed as an anticancer agent in warm-blooded animals, e.g. rats, it may be used alone or in combination with a therapeutically effective amount of an antineoplastic agent commonly used in cancer therapy and with pharmaceutically acceptable carriers, the proportion of which is determined by the solubility and chemical nature of the compounds, chosen route of administration and standard biological practice. For example, an antineoplastic effective amount of the antibiotic may be administered alone or in combination orally in solid form containing such excipients as starch, sugar, certain types of clay and so forth. Similarly, such an amount may also be administered orally in the form of solutions or suspensions, or the antibiotic may be injected parenterally alone or in combination. For parenteral administration the antibiotic may be used alone or in combination in the form of a sterile solution or suspension containing other solutes or suspending agents, for example, enough saline or glucose to make the solution isotonic, bile salts, acacia, gelatin, sorbitan monooleate, polysorbate 80 (oleate esters of sorbitol and its anhydrides co-polymerized with ethylene oxide) and the like.

When utilizing rapamycin alone or in combination with a therapeutically effective amount of an antineoplastic agent commonly used in cancer therapy for the treatment of tumors, the total dose of active agent can range from 0.01 to 250 mg per kg of body weight per day with a preferred dosage range from 0.1 to 50 mg per kg of body weight per day. However, as the dosage of rapamycin to be administered by the method of this invention will of course vary with the tumor or cancer and tolerance of the mammal, and with the nature of the other antineoplastic agents used in combination. The schedule of dosing can range from one to five times per day to a single dose given every two to ten days. Increasing the frequency of administration is expected to reduce the amount of active drug needed per dose. Such dosages and scheduling of administration must be determined on an individual basis, depending upon the tumor or cancer, nutritional state of the mammal, age of the mammal, toxicity in each individual, and with the nature of the other antineoplastic agents used in combination, etc.

Rapamycin was evaluated in several National Cancer Institute standard tumor test procedures. The results showed that rapamycin reduces tumor size in and prolongs the survival time of tumor-bearing mammals. More specifically, rapamycin is useful for controlling the following carcinogenic tumors in standard mammalian tumor models: lymphatic leukemia, colon, mammary, melanocarcinoma and ependymoblastoma. The effectiveness of rapamycin in this respect was demonstrated in the laboratory with rodents having transplanted tumors. Details of methods used to evaluate this effect are described in various publications; for example, R. I. Geran et al., Cancer Chemother. Rep., Part 3, 3, (No. 2) 1–103 (1972) and references therein. In addition, the protocols for the antitumor tests are available from the National Cancer Institute, Bethesda, Md., U.S.A. These models have been adopted by the National Cancer Institute as standard test procedures for predicting clinical activity of new chemotherapeutic agents.

Tables 1 to 6 show the effects of therapy with rapamycin on various tumors or cancers in rodents. More specifically, Table 1 shows the prolongation of survival time of female $CDF_1$ mice implanted with lymphatic leukemia P388 by administering rapamycin; Table 2 shows the reduction in size of colon 38 tumors in female $BDF_1$ mice by administering rapamycin; Table 3 shows the prolongation of survival time of male $CDF_1$ mice implanted with colon 26 tumors by administering rapamycin; Table 4 shows the reduction in size of $CD8F_1$ mammary tumors in male $CD8F_1$ rats by administering rapamycin; Table 5 shows the prolongation of survival time of female $BDF_1$ mice implanted with B16 melonocarcinoma by administering rapamycin; and Table 6 shows the prolongation of survival time of male Swiss mice implanted with ependymoblastoma by administering rapamycin.

TABLE 1

Effect of Rapamycin on Survival Time of $CDF_1$ Mice Implanted with Lymphatic Leukemia P-388 (ascetic)

| Dose/Inj. mg/kg | Ave. Wt. Difference of Animals (T-C, g) | Survivors on Day 5 | MST days T | MST days C | T/C% MST |
|---|---|---|---|---|---|
| 400 | −1.9 | 6/6 | 14.1 | 10.2 | 138 |
| 200 | −2.4 | 6/6 | 13.1 | 10.2 | 128 |
| 100 | −1.6 | 6/6 | 13.7 | 10.2 | 134 |
| 50 | −1.9 | 6/6 | 14.3 | 10.2 | 140 |
| 25 | −1.6 | 6/6 | 13.9 | 10.2 | 136 |
| 12.5 | −0.6 | 6/6 | 13.9 | 10.2 | 136 |

Treatment:
Nine intraperitoneal injections starting on day one in a vehicle of saline with Tween-80 [Trade Mark for a derivative of Z-sorbitan mono-9-octadecenoate poly-(oxy-1,2-ethanediyl)].
Evaluation:
T/C% = Median Survival Time (MST) in days of treated animals (T)/control animals (C) × 100. A T/C% of 125 or greater is considered as a significant prolongation of host survival. Evaluation done on day 30.

TABLE 2

Effect of Rapamycin on Colon 38 Tumor Weight in Mice

| Dose/Inj. mg/kg | Ave. Wt. Difference of Animals (T-C, g) | Survivors on Day 5 | MTW mg T | MTW mg C | T/C% MTW |
|---|---|---|---|---|---|
| 400 | −3.4 | 10/10 | 188 | 810 | 23 |
| 200 | −2.0 | 10/10 | 209 | 810 | 25 |
| 100 | −0.8 | 10/10 | 272 | 810 | 33 |
| 50 | −0.8 | 9/10 | 320 | 810 | 39 |
| 25 | −0.4 | 10/10 | 368 | 810 | 45 |
| 12.5 | 0.4 | 10/10 | 368 | 810 | 45 |

Treatment:
Single intraperitoneal injection on days 2, 9 and 16 in a vehicle of saline with Tween 80.
Evaluation:
T/C% = Median tumor weight (MTW) estimated from tumor diameter of treated animals (T)/control animals (C) × 100. A T/C% of 42 or less is considered as a significant inhibitor of tumor growth. Evaluation done on day 20.

TABLE 3

Effect of Rapamycin on Survival Time of $CDF_1$ Mice Implanted with Colon 26 Tumor

| Dose/Inj. mg/kg | Ave. Wt. Difference of Animals (T-C, g) | Survivors on Day 5 | MST days T | MST days C | T/C% MST |
|---|---|---|---|---|---|
| 400 | −2.4 | 10/10 | 26.3 | 19.1 | 137 |
| 200 | −1.8 | 10/10 | 25.8 | 19.1 | 135 |
| 100 | −1.4 | 10/10 | 29.0 | 19.1 | 151 |
| 50 | −0.8 | 10/10 | 30.6 | 19.1 | 160 |
| 25 | −0.3 | 10/10 | 30.3 | 19.1 | 158 |

TABLE 3-continued

Effect of Rapamycin on Survival Time of $CDF_1$ Mice Implanted with Colon 26 Tumor

| Dose/Inj. mg/kg | Ave. Wt. Difference of Animals (T-C, g) | Survivors on Day 5 | MST days T | MST days C | T/C% MST |
|---|---|---|---|---|---|
| 12.5 | 0.3 | 10/10 | 30.4 | 19.1 | 159 |

Treatment:
Single intraperitoneal injection on days 1, 5 and 9 in a vehicle of saline with Tween-80.
Evaluation:
T/C% = Median survival time (MST) in days of treated animals (T)/control animals (C) × 100. A T/C% of 125 or greater is considered as a significant prolongation of host survival. Evaluation done on day 60.

TABLE 4

Effect of Rapamycin on $CD8F_1$ Mammary Tumors in $CD8F_1$ Rats

| Dose/Inj. mg/kg | Average Net Wt. Difference of Animals (T-C, g) | Survivors on Day 5 | MTW days T | MTW days C | T/C% MTW |
|---|---|---|---|---|---|
| 400 | −6.6 | 4/10 | 0 | 3200 | — |
| 200 | −6.5 | 10/10 | 323 | 3200 | 10 |
| 100 | −4.8 | 10/10 | 448 | 3200 | 14 |
| 50 | −4.1 | 10/10 | 755 | 3200 | 23 |
| 25 | −2.4 | 10/10 | 825 | 3200 | 25 |
| 12.5 | −0.8 | 10/10 | 928 | 3200 | 29 |

Treatment:
Single intraperitoneal injection on days 1, 8, 15, 22 and 29 in a vehicle of saline with Tween-80.
Evaluation:
T/C% = Median tumor weight (MTW) estimated from tumor diameter of treated animals (T)/control animals (C) × 100. A T/C% of 42 or less is considered as a significant inhibitor of tumor growth. Evaluation done on day 30.

TABLE 5

Effect of Rapamycin on B16 Melanocarcinoma in $BDF_1$ Mice

| Dose/Inj. mg/kg | Average Net Wt. Difference of Animals (T-C, g) | Survivors on Day 5 | MST days T | MST days C | T/C% MST |
|---|---|---|---|---|---|
| 400 | −3.3 | 10/10 | 22.0 | 20.1 | 109 |
| 200 | −1.5 | 10/10 | 22.3 | 20.1 | 110 |
| 100 | −1.2 | 10/10 | 28.0 | 20.1 | 139 |
| 50 | −0.7 | 10/10 | 25.3 | 20.1 | 125 |
| 25 | 0.1 | 10/10 | 28.0 | 20.1 | 139 |
| 12.5 | 0.1 | 10/10 | 29.0 | 20.1 | 144 |

Treatment:
Single intraperitoneal injection on each of days 1 through 9 in a vehicle of saline with Tween-80.
Evaluation:
T/C% = Median Survival Time (MST) in days of treated animals (T) control animals (C) × 100. A T/C% of 125 or greater is considered as a significant prolongation of host survival. Evaluation done on day 60.

TABLE 6

Effect of Rapamycin on Ependymoblastoma in Swiss Mice

| Dose/Inj. mg/kg | Average Net Wt. Difference of Animals (T-C, g) | Survivors on Day 5 | MST days T | MST days C | T/C% MST |
|---|---|---|---|---|---|
| 200 | −3.3 | 10/10 | 44.0 | 18.1 | 243 |
| 100 | −2.2 | 10/10 | 26.0 | 18.1 | 143 |
| 50 | −1.3 | 9/10 | 34.0 | 18.1 | 187 |
| 25 | −2.0 | 10/10 | 34.0 | 18.1 | 187 |
| 12.5 | −1.0 | 10/10 | 32.3 | 18.1 | 178 |

Treatment:
Single intraperitoneal injection on each of days 1 through 9 in a vehicle of saline with Tween-80.
Evaluation:
T/C% = Median Survival Time (MST) in days of treated animals (T) control animals (C) × 100. A T/C% of 125 or greater is considered as a significant prolongation of host survival. Evaluation done on day 60.

The standard animal models used can be divided into two types based on how the results are expressed. Results can be expressed as a comparison of the median survival time for mammals in the treated (T) group (those treated with rapamycin) versus the median survival time for mammals in the untreated control (C) group. The result is given as a percentage of T/C; a high percent T/C indicates that the compound that was tested was effective in treating the malignant neoplasm that was evaluated. Statistically significant results are observed at either 125 or 130% T/C, depending on the neoplasm that was evaluated. Alternatively, the results of certain tests for solid tumors can be expressed based on the tumor weight of the solid tumor after the evaluation period. The tumor weight in the test (T) animals is compared with the tumor in the control (C) animals and the results are expressed as a percent T/C. When results are expressed as a function of tumor weight, a low % T/C indicates effective treatment of the neoplasm, as the tumors in the test animals are smaller than tumors in the untreated control animals. A percent T/C of less than 42 is considered to be statistically significant.

The results of the above described National Cancer Institute standard tumor test procedures demonstrate rapamycin's antineoplastic activity in mammals. As such rapamycin is useful in treating malignant neoplasms. Treating broadly includes, but is not limited to, inhibiting the proliferation of malignant cells, controlling the growth of malignant neoplasms, reducing the size of malignant neoplasms, eradicating malignant neoplasms, prolonging the survival time of said mammal, killing malignant cells, and adversely affecting malignant cells. Preferred embodiments of this invention, that are described below, are based on the specific types of malignant neoplasms that rapamycin has been shown to be effective in treating. The scope of this invention, however, is not limited to these specific embodiments, as other neoplasms that rapamycin is effective in treating will be apparent to one skilled in the art.

Based on the ability of rapamycin to significantly inhibit tumor growth in the Colon 38 standard test procedure, as seen by a reduction in tumor size, and increase survival time of the host mammal in the Colon 26 standard test procedure, rapamycin is useful in treating mammalian carcinomas of the colon and rectum. The use of rapamycin in treating colon cancer is covered in U.S. Pat. No. 4,885,171.

In the $CD8F_1$ mammary tumor test procedure, rapamycin caused a reduction in tumor size at doses of up to 200 mg/kg. Mammary tumors were reduced in weight by 71% at 12.5 mg/kg and by 90% at a dose of 200 mg/kg, indicating an almost complete eradication of the mammary carcinoma. As such, rapamycin is useful in treating mammalian breast neoplasms.

A significant increase in survival time of the host mammal was observed in the B16 melanocarcinoma standard test procedure for mice that were treated with doses of up to 100 mg/kg. As such, rapamycin is useful in treating skin carcinomas such as basal cell carcinoma, squamous cell carcinoma, malignant melanoma, and the like.

The ependymoblastoma standard test procedure is predictive of a compound's ability to treat malignant central nervous system neoplasms. At a dose of 50 mg/kg, a % T/C of 187 was obtained, and at a dose of 200 mg/kg, a % T/C of 243 was obtained (median survival time of 44.0 days for mammals treated with rapamycin versus median survival time of 18.1 days for untreated control group). At all doses tested, rapamycin caused a significant increase in survival time of the host mammal in the ependymoblastoma standard test procedure, and is therefore useful in treating malignant central nervous system neoplasms. The extremely favorable results obtained in this test procedure also indicate that rapamycin is capable of reaching the intracranial neoplasm by crossing the blood brain barrier. Malignant central nervous system neoplasms describes a broad class of intracranial neoplasms which include, but are not limited to: intracranial meningiomas, sarcomas, gliomas, astrocytomas, medulloblastomas, schwannomas, ependymomas, meningiomas, germinomas, and the like.

Rapamycin was weakly active in the P-388 leukemia standard test procedure; a maximal % T/C of 140 was achieved at a dose of 50 mg/kg. When comparing these data to other data obtained for other anti-leukemic compounds described in the literature, rapamycin is not felt to be useful in treating higher mammalian leukemias.

Rapamycin also can be used to produce beneficial effects in the treatment of malignant neoplasms when combined with a therapeutically effective amount of an antineoplastic agent commonly used in cancer therapy. Such antineoplastic agents include the alkylating agents, for example, busulfan, chlorambucil, cyclophosphamide, mechlorethamine hydrochloride, melphalan, pipobroman, thiotepa and uracil mustard; antimetabolites, for example, cytarabine, fluorouracil, floxuridine, mercaptopurine, methotrexate and thioguanine; miscellaneous anticancer agents, for example, dacarbazine, hydroxyurea, mitotane, procarbazine hydrochloride, quinacrine hydrochloride, vinblastine sulfate and vincristine sulfate; estogens, for example, chlorotrianisene, conjugate estogens (e.g. PREMARIN ®), diethylstilbestrol and the like; androgens, for example, methyltestosterone, testosterone and the like; adrenal corticosteroids, for example, prednisone and the like; progestagens, for example, megestrol, hydroxyprogesterone caproate and the like; radioactive isotopes; and antibiotics, for example, bleomycin sulfate, doxorubicin hydrochloride and the like. Suitable methods of administration, compositions and dosages of the antineoplastic agents are described in medical textbooks; for instance, "PHYSICIANS' DESK REFERENCE", 32nd ed., Medical Economics Co., Oradell, N.J. U.S.A., 1978 and "AMA DRUG EVALUATIONS", 3rd ed. PSG Publishing Company, Inc., Littleton, Mass., U.S.A. pp 1106-1151, 1977. When used in combination, rapamycin is administered as described previously; however, a lower dose can be used for efficacious results.

We claim:

1. A method of treating a malignant neoplasm selected from the group consisting of a mammary carcinoma, a skin carcinoma, and a central nervous system neoplasm in a mammal in need thereof which comprises administering an antineoplastic amount of rapamycin to said mammal orally or parenterally with the proviso that said malignant neoplasm has not been transplanted into said mammal.

2. The method of claim 1 wherein the skin carcinoma is selected from the group consisting of a basal cell carcinoma, squamous cell carcinomas, and malignant melanoma.

3. The method of claim 1 wherein the central nervous system neoplasm is an intracranial neoplasm selected from the group consisting of a meningioma, sarcoma, glioma, astrocytoma, medulloblastoma, schwannoma, ependymoma, meningioma, and germinoma.

4. A method of inhibiting the proliferation of malignant cells selected from the group consisting of a mammary carcinoma, a skin carcinoma, and a central nervous system neoplasm in a mammal in need thereof which comprises administering an antineoplastic amount of rapamycin to said mammal orally or parenterally with the proviso that said malignant cells have not been transplanted into said mammal.

5. The method of claim 4 wherein the skin carcinoma is selected from the group consisting of a basal cell carcinoma, squameous cell carcinomas, and malignant melanoma.

6. The method of claim 4 wherein the central nervous system neoplasm is an intracranial neoplasm selected from the group consisting of a meningioma, sarcoma, glioma, astrocytoma, medulloblastoma, schwannoma, ependymoma, meningioma, and germinoma.

7. A method of reducing the size of a malignant neoplasm selected from the group consisting of a mammary carcinoma, a skin carcinoma, and a central nervous system neoplasm in a mammal in need thereof which comprises administering an antineoplastic amount of rapamycin to said mammal orally or parenterally with the proviso that said malignant neoplasm has not been transplanted into said mammal.

8. The method of claim 7 wherein the skin carcinoma is selected from the group consisting of a basal cell carcinoma, squameous cell carcinomas, and malignant melanoma.

9. The method of claim 7 wherein the central nervous system neoplasm is an intracranial neoplasm selected from the group consisting of a meningioma, sarcoma, glioma, astrocytoma, medulloblastoma, schwannoma, ependymoma, meningioma, and germinoma.

10. A method of eradicating a malignant neoplasm selected from the group consisting of a mammary carcinoma, a skin carcinoma, and a central nervous system neoplasm in a mammal in need thereof which comprises administering an antineoplastic amount of rapamycin to said mammal orally or parenterally with the proviso that said malignant neoplasm has not been transplanted into said mammal.

11. The method of claim 10 wherein the skin carcinoma is selected from the group consisting of a basal cell carcinoma, squameous cell carcinomas, and malignant melanoma.

12. The method of claim 10 wherein the central nervous system neoplasm is an intracranial neoplasm selected from the group consisting of a meningioma, sarcoma, glioma, astrocytoma, medulloblastoma, schwannoma, ependymoma, meningioma, and germinoma.

* * * * *